(12) United States Patent
Göllner et al.

(10) Patent No.: US 10,779,830 B2
(45) Date of Patent: Sep. 22, 2020

(54) CONNECTION SYSTEM FOR THE DETACHABLE FIXATION OF A HOLLOW CYLINDRICAL COMPONENT AT A RECESS

(75) Inventors: Manfred Göllner, Berlin (DE); Daniel Marcinowski, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 1228 days.

(21) Appl. No.: 14/117,428

(22) PCT Filed: May 15, 2012

(86) PCT No.: PCT/EP2012/002150
§ 371 (c)(1),
(2), (4) Date: Jun. 26, 2014

(87) PCT Pub. No.: WO2012/156101
PCT Pub. Date: Nov. 22, 2012

(65) Prior Publication Data
US 2014/0316426 A1    Oct. 23, 2014

Related U.S. Application Data

(60) Provisional application No. 61/486,442, filed on May 16, 2011.

(30) Foreign Application Priority Data

May 16, 2011 (EP) ..................................... 11075087

(51) Int. Cl.
*A61B 17/11* (2006.01)
*A61M 1/10* (2006.01)
(Continued)

(52) U.S. Cl.
CPC ............ *A61B 17/11* (2013.01); *A61B 17/1114* (2013.01); *A61M 1/10* (2013.01);
(Continued)

(58) Field of Classification Search
CPC ........ A61M 1/1008; A61M 1/10; A61M 1/12; F16L 37/0985; F16L 2017/1107;
(Continued)

(56) References Cited

U.S. PATENT DOCUMENTS 3,527,485 A    9/1970  Goward et al.
3,919,722 A *  11/1975 Harmison ........... A61M 1/1037
                                                    623/3.16

(Continued)

FOREIGN PATENT DOCUMENTS

| CN | 101442945 A | 5/2009 |
|----|-------------|--------|
| CN | 2010/0185279 A1 | 7/2010 |
| WO | WO 2007/084340 A2 | 7/2007 |

OTHER PUBLICATIONS

Chinese Office Action with English translation, dated Sep. 6, 2019, pp. 1-16, issued in Chinese Patent Application No. 201710088924. 5, China National Intellectual Property Administration, Beijing, China.

*Primary Examiner* — Jing Rui Ou
(74) *Attorney, Agent, or Firm* — Brinks Gilson & Lione (57) ABSTRACT

An easily detachable connection of a hollow cylindrical component, such as a graft, at a recess in tissue, such as a heart or a blood vessel, an annular element, a guide element and a spring element are provided, which are secured by way of a suture ring at the body part and at the hollow cylindrical component, and which permit an easily disengageable mutual locking by way of the spring element. To this end, the annular element comprises a groove extending around the periphery thereof, into which the spring element plunges for locking.

17 Claims, 7 Drawing Sheets

(51) Int. Cl.
  *F16L 37/098* (2006.01)
  *A61F 2/06* (2013.01)
  *A61M 1/12* (2006.01)

(52) U.S. Cl.
  CPC ....... *A61M 1/1008* (2014.02); *F16L 37/0985* (2013.01); *A61B 2017/1107* (2013.01); *A61F 2/064* (2013.01); *A61M 1/12* (2013.01)

(58) Field of Classification Search
  CPC ...... A61F 2/064; A61B 17/11; A61B 17/1114; A61B 2017/1107
  See application file for complete search history.

(56) References Cited

U.S. PATENT DOCUMENTS

| | | | |
|---|---|---|---|
| 5,089,014 A * | 2/1992 | Holfert | A61B 17/11 623/1.24 |
| 5,314,469 A * | 5/1994 | Gao | A61M 1/1046 600/16 |
| 5,374,088 A | 12/1994 | Moretti et al. | |
| 6,001,056 A * | 12/1999 | Jassawalla | A61F 2/2412 600/16 |
| 6,146,325 A * | 11/2000 | Lewis | A61M 1/1037 600/16 |
| 6,319,231 B1 | 11/2001 | Andrulitis | |
| 6,346,071 B1 * | 2/2002 | Mussivand | A61M 1/1037 600/16 |
| 2002/0095210 A1 * | 7/2002 | Finnegan | A61F 2/064 623/3.26 |
| 2003/0023255 A1 | 1/2003 | Miles et al. | |
| 2005/0033107 A1 * | 2/2005 | Tsubouchi | A61M 1/10 600/6 |
| 2007/0084340 A1 | 4/2007 | Dou et al. | |
| 2007/0134993 A1 | 7/2007 | Tamez et al. | |
| 2007/0167969 A1 | 7/2007 | Pandey | |
| 2010/0185279 A1 | 7/2010 | Shad | |
| 2011/0118766 A1 * | 5/2011 | Reichenbach | A61M 1/10 606/153 |
| 2012/0226096 A1 * | 9/2012 | Callaway | A61M 1/10 600/16 |

\* cited by examiner

CONNECTION SYSTEM FOR THE DETACHABLE FIXATION OF A HOLLOW CYLINDRICAL COMPONENT AT A RECESS

CROSS-REFERENCE TO RELATED APPLICATIONS

This application is a 371 nationalization of PCT/EP2012/002150, which in turn claims benefit of European patent application 11075087.4 filed on May 16, 2011 and U.S. provisional application 61/486,442 filed on May 16, 2011.

BACKGROUND

The invention applies to the field of mechanical science and especially connection technology, and relates more particularly to the establishment of a connection comprising hollow cylindrical components. The invention can be used particularly advantageously in the field of medical technology.

In medical technology, more particularly in operations involving blood circulation, it is often necessary to connect hollow cylindrical components in the form of cannulas, grafts, tube connectors and the like to one another or to parts of a patient's body, such as blood vessels or organs.

A typical application is the connection of a graft to a hole in a heart wall or a large blood vessel, wherein a suture ring is connected to organ tissue by way of a sutured connection and appropriate hollow cylindrical components are then connected to the suture ring.

Appropriate hollow cylindrical components can also extend partially into the opening of the pertinent body part, such as into the heart wall or into the opening of a blood vessel, at least to a certain extent.

Diverse variants of the connection of hollow cylindrical components to the opening of a body part of a patient's body are known from the prior art. For example, document US 2007/0134993 A1 shows a suture ring that can be connected to bodily tissue in the manner of a flange, wherein a tube connector is fixedly connected to the suture ring. The tube connector has a longitudinal slot bridged by a screw, thereby enabling the connector to be fixedly clamped radially on an inserted tube piece by tightening the screw.

A very similar configuration is shown in US 2007/0167969 A1. In that case, however, the focus is on a tool for creating an opening in a body part in a targeted manner.

Document WO 2007/084340 A2 (see FIG. 1 in combination with text page 6) likewise makes known a suture ring comprising a clamping ring secured thereto, wherein the clamping ring can be compressed radially by way of a screw located on the periphery thereof.

Since space that may not be available during an operation is required to tighten the screws described in the prior art, and since time is required to perform said tightening and it is generally difficult to inspect the establishment of a clamped connection of this type, the problem addressed by the present invention is that of creating a connection system for such cases, which makes it possible to easily and detachably connect a hollow cylindrical component to a recess and which can be implemented using the simplest possible structural means.

Document U.S. Pat. No. 6,319,231 B1 makes known a connection system, by way of which a cannula can be connected to a connector, wherein the two parts are mutually locked by way of a groove/spring connection to a retaining ring that is simultaneously positioned in an outer groove of one part and in an inner groove of the other part. The retaining ring is released by tightening in the circumferential direction.

Document US 2003/0023255 A1 likewise makes known a groove/spring connection for a cannula for a medical application, wherein the type of creation and release of the lock is not discussed in detail.

SUMMARY

In the connection system for detachably affixing a hollow cylindrical component at a recess in a part of a patient's body, an annular element is therefore provided according to the invention that comprises a groove that extends azimuthally around the outer jacket surface thereof, at least in sections, and a guide element, which can be displaced in the axial direction of the cylindrical component with respect to the annular element before fixation. The guide element and the annular element can be inserted into one another at least partially in the axial direction, and so they overlap partially in the axial direction. A spring element is also provided, which is movably guided in the guide element exclusively perpendicular to the axial direction and plunges at least partially into the groove of the annular element. The spring element therefore affixes the annular element and the guide element against one another in the axial direction. To affix the hollow cylindrical component at the recess, either the annular element or the guide element is connected or coupled to the hollow cylindrical component, and the other of the two bodies is connected or coupled to the edge of the recess.

In this manner the hollow cylindrical component can be detachably secured at the recess by way of the annular element and the guide element and the spring element, which locks them.

The annular element can have a cylindrical design, for example, and the groove extending around the circumference thereof can also extend around the entire circumference as a complete annular groove.

The annular groove can have a cross section that is rectangular, V-shaped or U-shaped. By way of a bevel of the walls of the annular groove, it is also possible to remove the hollow cylindrical component if excessive axial forces occur in that the spring element is pushed out of the groove and the connection between the annular element and the guide element is forcibly disengaged.

The guide element can have a cylindrical bore hole for the hollow cylindrical component and, additionally, a cavity for guidance of the spring element. To this end, the guide element can substantially comprise two plate-type, interconnectable partial bodies, which are made of titanium, for example. They can be welded to one another.

The spring element can be stiff or resilient, but it must be sized such that it can plunge, as a spring, at least partially into the groove of the annular element.

Each of the components, that is, the annular element and the guide element and the spring element, can be made of a metal, preferably a titanium alloy, or of a plastic, such as a hard silicone, a polyethylene or a polyurethane. It is also possible for one or more components to be made of a first one of these materials and for one of the other components to be made of another material.

The annular element and the guide element are connected or coupled either to the hollow cylindrical component or to the edge of the recess, respectively. This means that the respective components are connected indirectly or directly to the hollow cylindrical component and the edge of the recess. It is therefore possible to provide one more component in each case, which is connected to the hollow cylindrical component or to the edge of the recess, and to which the annular element or the guide element is respectively connected or coupled. In the connection to the hollow cylindrical component, the annular element and the guide element can displaceable thereon in the axial direction to a limited extent, for example, wherein the limitation of the displaceability can be implemented by way of a stop secured to the component, for example.

Advantageously, according to the invention, the spring element can be displaceably guided, non-deformed per se, in the guide element. The spring element has at least one first position within the guide element, in which it plunges into the groove of the annular element after the guide element and the annular element are inserted into one another, and at least one second position in which the spring element does not plunge into the groove of the annular element. The spring element can be pivoted, rotated or displaced between these positions.

For example, the outer contour of the cross section of the annular element can be elliptical, and the spring element can have a corresponding elliptical opening into which the annular element fits in the first orientation thereof. If the annular element and the spring element are then rotated opposite one another about the axis of the hollow cylindrical component, the spring element can plunge into the annular groove of the annular element and establish the lock. To this end, the spring element comprises an operating lever, which protrudes from the guide element and can be operated from the outside to rotate the spring element.

Advantageously, the spring element can also be elastically deformable within the guide element between a locked state and an unlocked state in which it does not plunge into the groove of the annular element. In this case as well, the spring element is advantageously designed such that it protrudes from the guide element at least partially in such a way that the elastic deformation can be induced manually from the outside.

The spring element can be pressed at one side within the guide element radially with respect to the axial direction of the hollow cylindrical component against a fixed stop, thereby permitting it to expand radially. To this end, the spring element can protrude on exactly one side, for example, radially beyond and/or out of the guide element and can be pressed into the guide element radially from this side. This simplifies handling, more particularly the closure and release of the connection during surgery, for example, since the connection system need only be accessible from one radial side for actuation. It suffices to hold the guide element and press the spring element against it.

According to a further advantageous embodiment of the invention, the spring element comprises elastically resilient components made of a plastic or a metal, more particularly being made entirely of such a resilient material.

According to a further embodiment of the invention, the spring element is elastically expandable radially relative to the axial direction of the cylindrical element.

By way of the radial deformability, the spring element can be advantageously compressed in a first radial direction and, simultaneously, can be radially expanded perpendicular thereto. In this manner, it can be elastically deformed by way of radial pressure in such a way that, in a first shape, it can be slid over the annular element and, in a second shape, it plunges at least partially into the groove of the annular element.

To this end, the expansion of the annular spring element in a first direction can be greater than in a second direction that extends transversely to the first direction.

The spring element can be designed, for example, as an elliptically shaped, closed retaining clip or a substantially diamond-shaped or hexagonally shaped retaining clip. In this case, the spring element can be expanded or compressed overall by the application of radial pressure on two opposing sides.

To permit meaningful use with such a spring element, the cross section of the annular element must be shaped such that the spring element can be slid over the annular element in a first shape and, in a second shape, it plunges at least partially into the groove of the annular element. To this end, for example, the diameter of a circle inscribed in the annular spring element in the unloaded state is smaller than the outer diameter of the annular element.

In addition, according to an advantageous embodiment of the invention, the element that is connected or connectable to the edge of the recess is connected or connectable to a securing member that is directly connected or connectable to the edge. In this manner, an appropriate securing member can be connected to the edge of the recess by suturing, for example, or other common connecting techniques before the connection system is installed. Such a securing member is often a suture ring designed as felt or cloth, which can be connected to tissue of the patient's body by way of a threaded connection. The annular element or the guide element can be fixedly connected to the securing member before it is affixed to the tissue or at the edge of the recess. However, they can also be connected to the securing member by way of a clamp connection, an adhesive connection, or a threaded connection after securing at the edge of the recess.

According to a further advantageous embodiment of the invention, the securing member is a suture ring that can be secured to organic tissue at the edge of the recess by way of a sutured connection using thread.

It can also be provided that the securing member comprises a peripheral sealing lip, which is made of silicone, for example, at which the hollow cylindrical component extending therethrough seals. The sealing lip can be provided at an opening of the securing member and extend there into the interior of the opening. In this case, the sealing lip of the securing member seals outwardly at the cylindrical jacket surface of the hollow cylindrical component. It is then only necessary to establish the mechanical fixation of the hollow cylindrical component, wherein the seal integrity of the connection can be ensured exclusively by way of the sealing lip.

The securing member can comprise, for example, a suture ring made of titanium, on which a cloth/felt ring is slid from one side and a silicone ring comprising a sealing lip and a further cloth/felt ring is placed and secured from the other side.

The invention is shown in the following in a drawing with reference to an exemplary embodiment and is subsequently described.

BRIEF DESCRIPTION OF THE DRAWINGS

Shown are

FIG. 1 a heart wall comprising a suture ring secured thereto, shown schematically in a section, FIG. 2 the arrangement depicted in FIG. 1 having a tube connector inserted therein, FIG. 3 an alternative approach to securing a tube connector in an opening in a heart wall, FIG. 4 a connection system according to the invention, in the non-fixed state, shown schematically in a longitudinal view, FIG. 5 the arrangement depicted in FIG. 4, in the fixed state, FIG. 6 a part of a guide element, FIG. 7 the part of the guide element depicted in FIG. 6, comprising an inserted spring element, FIG. 8 the complete guide element comprising a spring element, FIG. 9 a top view of a section of the guide element comprising a spring element in the locked state, FIG. 10 a section as shown in FIG. 9 but comprising an elastically deformed and unlocked spring element, FIG. 11 two parts of a guide element in a three-dimensional exploded view, FIG. 12 an alternative guide element comprising a spring element that is merely displaceable, and FIG. 13 a further alternative guide element, likewise comprising a displaceable spring element.

DESCRIPTION OF PREFERRED EMBODIMENTS

Figure 1:
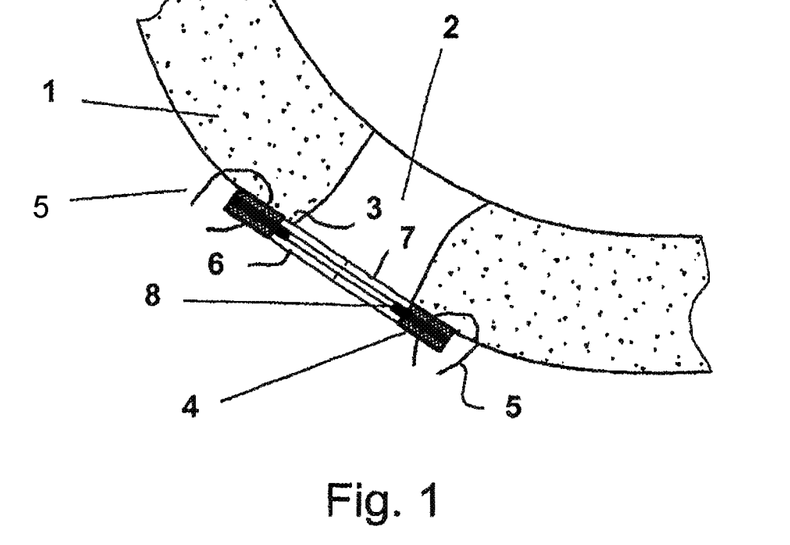

FIG. 1 shows, schematically, a part of a heart wall 1 having a continuous recess 2, which can also be formed artificially, for example, by punching or cutting into the heart wall.

A suture ring 4 is placed onto the edge 3 of the recess 2, which can be connected to the organic tissue of the heart wall 1 by way of a peripheral surgical suture using a thread 5. Such a suture ring can be made of a felt-type fabric, for example, which can be easily penetrated by a suture needle. In the exemplary embodiment shown, the suture ring 4 comprises a first fabric layer 6, a second fabric layer 7 and, disposed therebetween, a sealing layer 8 having a radially inwardly protruding sealing lip made of silicone.

The suture ring 4 serves to establish and simplify a reliable connection of a conduit element or tube element at the heart wall 1. The conduit element can be a pump connector, which may be part of a pump housing.

Figure 2:
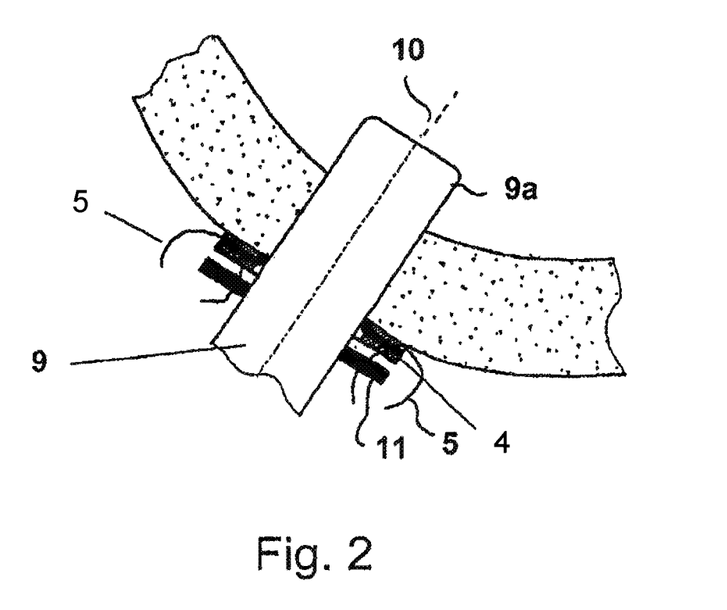

FIG. 2 shows a cylindrical object that has been inserted into the recess 2, which is typically in the form of a conduit element or a hollow cylindrical graft 9. It serves to create a conduit channel from the interior of the heart or another organ to a desired other point. A graft is usually flexible, although it can also comprise a stiff end that can be inserted into a recess 2. The end 9a is also intended to be freely rotatable in the recess about the longitudinal axis 10 thereof. The end 9a of the graft comprises a securing flange 11, which can likewise be made of a fabric or can contain a fabric, and which can be sutured to the suture ring 4 in order to affix the end of the graft in the recess 2 at the suture ring.

The flange can also be made of a hard material, more particularly a metal or a hard plastic, and can have openings that permit passage of the thread 5 for fixation at the suture ring.

Figure 3:
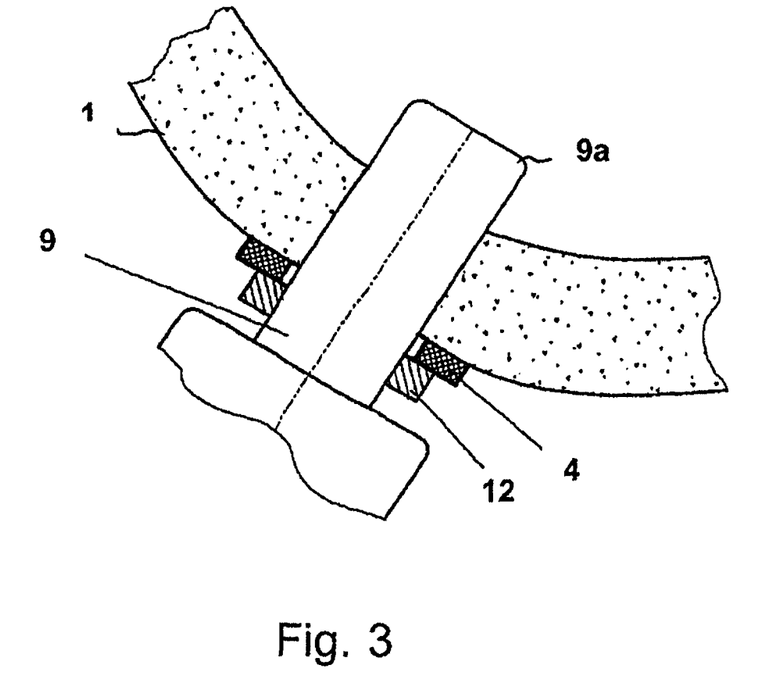

FIG. 3 shows another attachment method, in which a clamping ring 12 is fixedly connected directly to the suture ring 4, said clamping ring being slotted in the longitudinal direction and therefore radially expandable to permit easy insertion of the end 9 of the graft. Once the end 9a of the graft has been positioned, the clamping ring 12 is tightened by way of a clamping screw or clamp, which are not shown in detail, that is, it is also compressed radially, in order to fix and securely position the end 9a. The clamping ring 12 can be sized such that it simultaneously seals.

However, operating a clamping mechanism for such a clamping ring 12 is complicated in surgical conditions, and simple disengagement of said connection would also be desirable.

Figure 4:
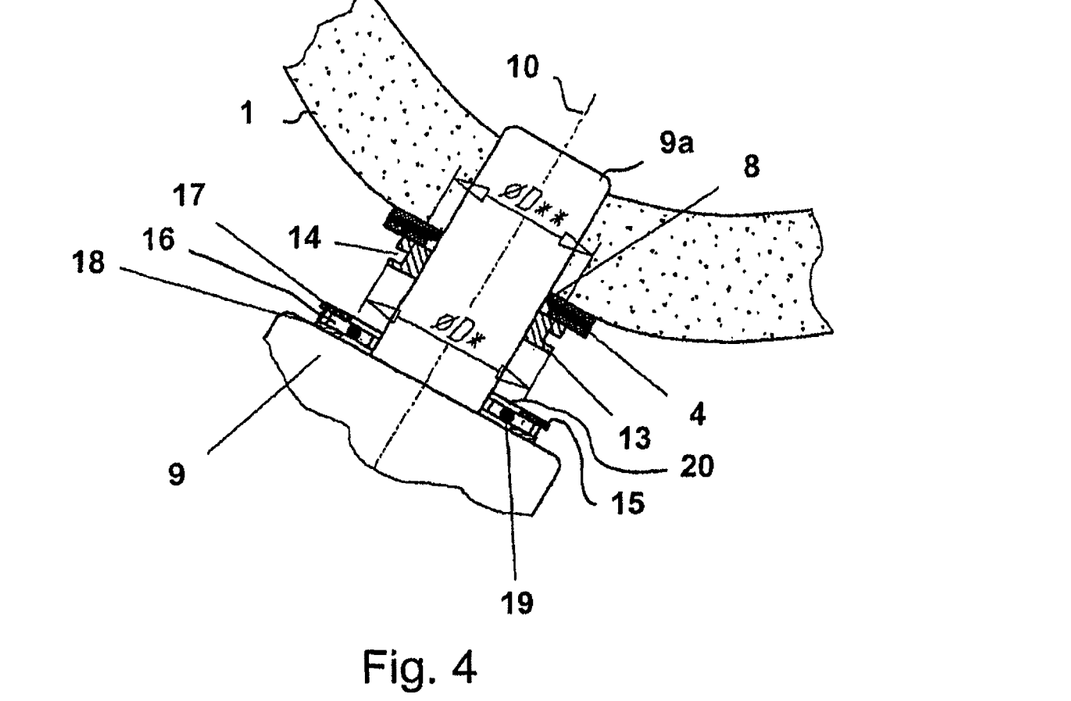

FIG. 4 shows an embodiment of a connection system according to the invention, with which the end 9 of a hollow cylindrical component is detachably securable in a recess of a heart wall 1, wherein the connection is likewise easy to engage and disengage.

To this end, a suture ring 4 connected to the heart wall 1 is provided in the depiction in FIG. 4, to which an annular element 13 is fixedly connected, which comprises a groove 14 that extends azimuthally around the outer jacket surface thereof. The cross section of the groove 14 is rectangular, although it could also be V-shaped or round.

Moreover, a guide element 15 is provided, which is fixedly connected to the hollow cylindrical component 19 and guides a spring element 19 in a cavity 16 between two front plates 17, 18.

The front plate 17 has a central recess 20, which is so large that at least a portion of the guide element 15 can be axially inserted onto the annular element 15.

To slide the guide element 15 in the axial direction of the cylinder axis 10 onto the annular element 13, the spring element 19 is deformed in such a way that it can likewise be slid over the annular element 13 and thereby elastically plunges radially into the groove 14. The spring element can be easily deformed by the application of manual force or by traveling up a bevel on the annular element. Since the spring element 19 is held in the guide element 15, it can mutually lock the annular element 13 and the guide element 15 in the axial direction of the axis 10.

Figure 5:
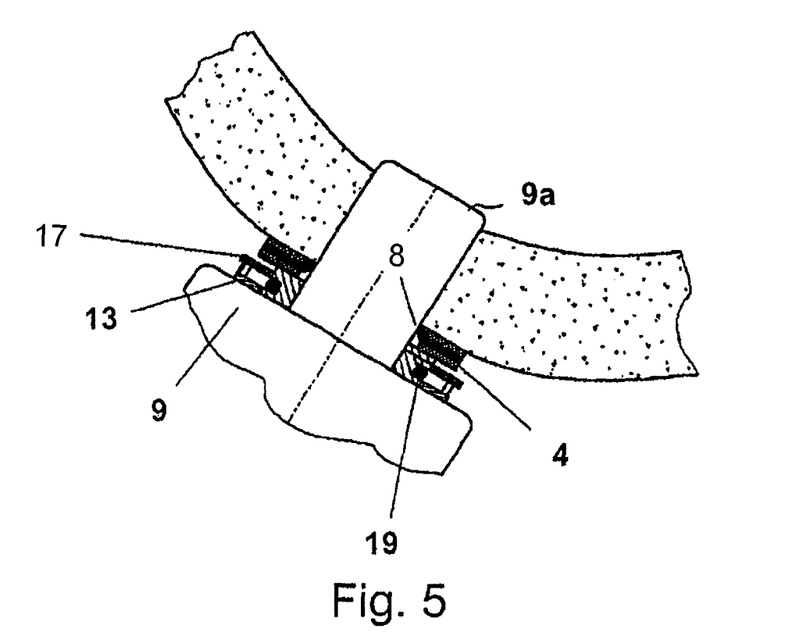

FIG. 5 shows, in detail, the connection state in the locked form, in which the spring element 19 has already snapped into the groove 14 of the annular element 13. The end 9 of the hollow cylindrical element is therefore fixed in the recess of the heart wall 1 by way of the suture ring 4 in an easily detachable manner. In principle, instead of fixing an annular element 13 at the suture ring and fastening the guide element 15 at the hollow cylindrical element, the reverse is also possible, that is, to replace the annular element 13 by the guide element and have it connected to the hollow cylindrical element, while, in this case, the guide element 15 is connected to the suture ring 4 or, in another manner, is connected directly to the edge of the recess 2 in the heart wall 1.

For the rest, the connection system can also be used in other organs or in blood vessels, for example, wherein the heart wall 1 would then be replaced by the wall of a blood vessel.

The hollow cylindrical element 9 can be typically made of a metal, more particularly a titanium alloy, or of a plastic, for example, a corrugated tube, wherein it can have a continuous cylindrical design having a constant diameter in the region in which it can be slid into the suture ring, in order to permit sealing of the sealing lip 8 at that point. Said end 9a of the element/graft can be made of different material, for example, than the remaining region, for example, of PTFE, polyurethane or a metal.

The hollow cylindrical element can be in the form, for example, of connector of a pump, more particularly a heart pump, or in the form of a pump tube that simultaneously forms a part of the pump housing.

The guide element 15 and the annular element 13 can preferably comprise a metal, more particularly a titanium alloy, for example the same alloy as the hollow cylindrical element 9, although in special cases it can also be made of a resistant plastic such as polyurethane, or of PTFE or polyethylene. The spring element 19 can likewise be made of one of the aforementioned materials, although it must be elastically deformable. The spring element 19 can be designed as a metal wire having appropriate elastic properties.

The spring element 19 is also intended to be shaped such that it protrudes from an opening provided on the periphery of the guide element 15 in such a way that it can be moved or compressed from that point.

Figures 6, 7, 8:
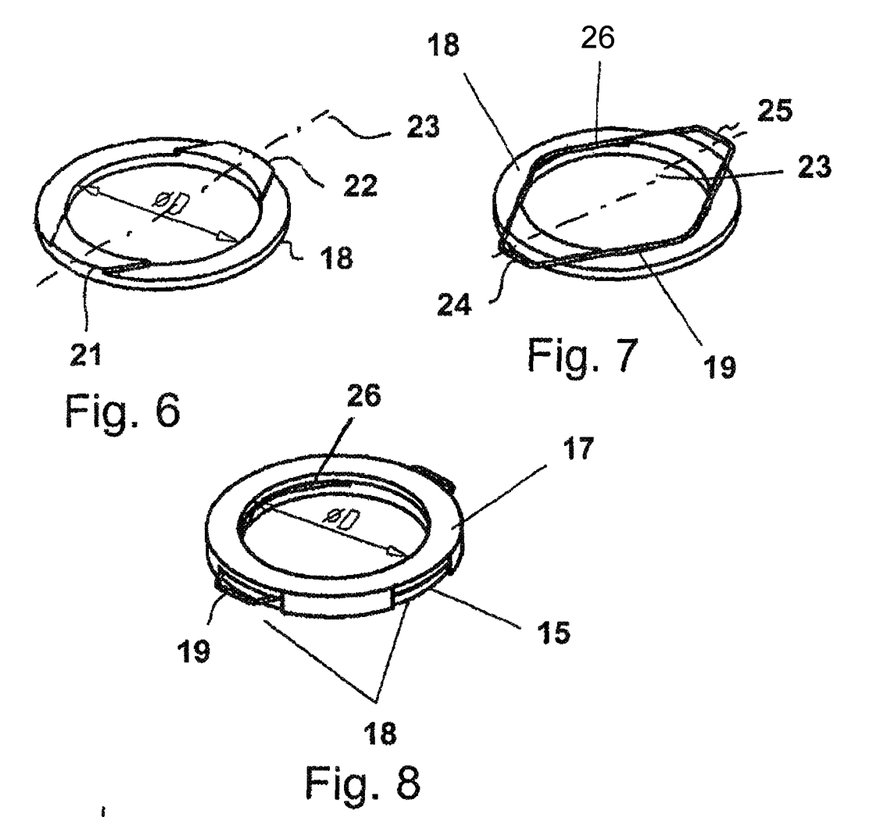

FIG. 6 shows, in a three-dimensional depiction, a front plate 18 of the guide element, which is made of a plastic, for example, is substantially shaped as a circular ring and comprises two thickened regions 21, 22, which lie opposite one another on the ring symmetrically with respect to an axis 23 that is a symmetry axis of the front plate 18. The height of the thickened regions 21, 22 can correspond approximately to or be slightly larger than the thickness of the spring element 19.

FIG. 7 shows the front plate 18 depicted in FIG. 6 comprising a spring element 19 placed thereon, which, in this case, is formed by a closed retaining clip having a diamond shape. The diamond shape of the spring element 19 has only two blunt regions 24, 25 which serve to improve grippability in the assembled state. The spring clip is retained by the thickened regions 21, 22 and is designed such that it can be compressed exclusively in the direction of the axis 23 and is expandable transversely to the axis 23 and, therefore, radially. To this end, the blunt ends 24, 25 can be gripped using two fingers and moved toward one another in order to expand the spring element 19.

FIG. 8 shows the guide element 15 in the assembled form comprising the first front plate 17 and the second front plate 18. The front plates 17, 18 are shaped such that, in the assembled state, they leave space between them for the spring element 19. More particularly, the first front plate 17 can lie on the thickened regions 21, 22. FIG. 8 shows the spring element 19 between the front plates 17, 18, which protrudes from openings at the outer jacket surface of the guide element and can be manually operated there. As shown at the point 26, the spring element 19 in the unloaded state protrudes into the inner central opening of the guide element. The guide element 15 can still be slid onto the annular element 13 by way of said inner opening when the spring element 19 is actuated. Once the sliding-on has been completed, the spring element 19 can be released, thereby permitting it to snap radially inwardly into the groove 14 of the annular element.

Figure 9:
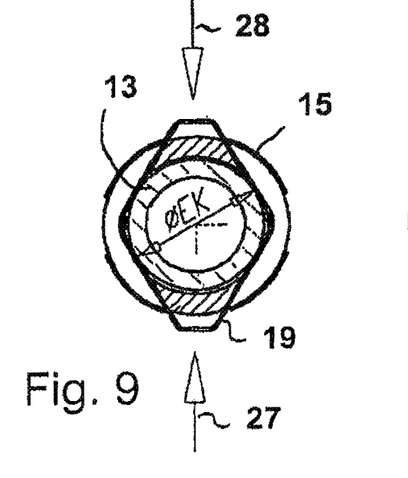

FIG. 9 shows, in a perpendicular top view, a section of the guide element 15 comprising an unactuated spring element 19. The actuating forces of the spring element are indicated by two arrows 27, 28. In addition to the guide element 15, the annular element 13 is also sketched in the interior thereof, wherein the spring element 19, in the top view, partially penetrates the annular element 13 since it is plunged into the circumferential groove thereof.

Figure 10:
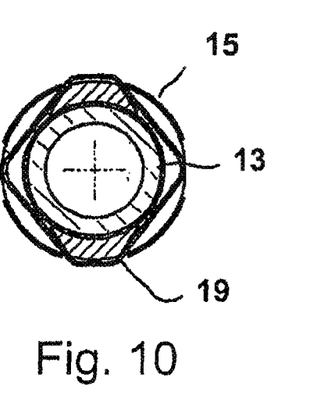

FIG. 10 shows, in contrast, the same section as in FIG. 9 with an actuated spring element 19 that has been expanded by the application of force to the extent that it does not radially touch the circumference of the annular element 13 at any point. In this position, the guide element 15 comprising the spring element 19 can be slid onto the annular element 13 and can be removed therefrom.

Figure 11:
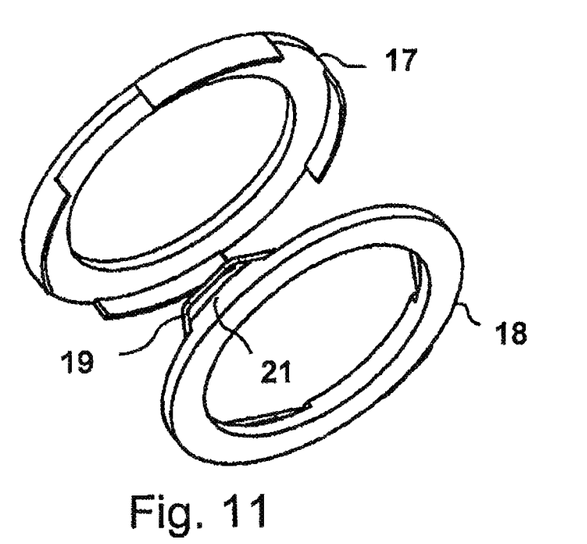

FIG. 11 shows, schematically, the interaction of the front plates 17, 18 before they are assembled to form a guide element. A thickened region 21 and the inserted spring element 19 are shown at the front plate 18.

Figure 12:
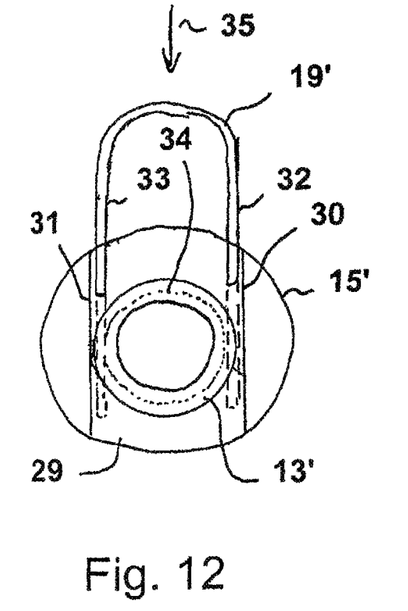

FIG. 12 shows an alternative embodiment of a guide element, an annular element and a spring element. The guide element 15' is shown comprising an annular element 13' located concentrically therein. The guide element 15' has a wide groove 29 or only two guide channels 30, 31 for the two arms 32, 33 of the spring element 19'. The spring element does not have to be expanded to be slid into the groove of the annular element 13', which is depicted by the dashed base 34 having the groove. The spring element 19' can be slid easily in the direction of the arrow 35 radially into the guide element 15' in order to plunge into the groove of the annular element and mutually lock the spring and the guide element. The guidance of the spring element 19' in the guide element 15' can be designed so tight that the spring element automatically becomes wedged in the guide element. However, the arms 32, 33 of the spring element 19' can also be designed so long that they pass through the guide element and can be secured on the other side by way of a snap ring.

Figure 13:
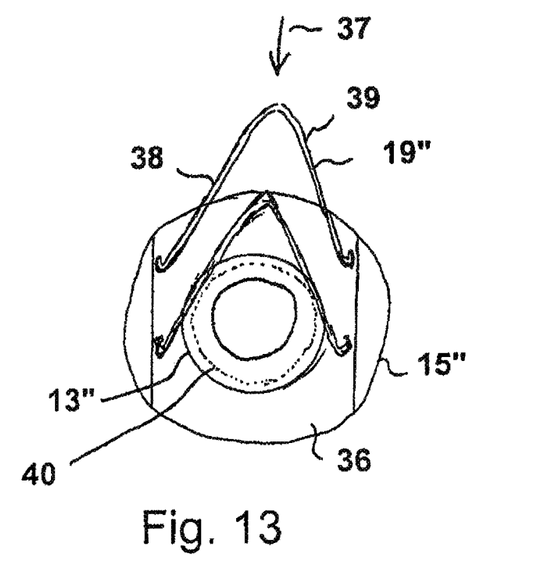

FIG. 13 shows a further embodiment of a guide element and a spring element comprising a guide element 15", which has a groove for receiving the V-shaped spring element 19". The spring element can be clamped in the groove 36 of the guide element 15" between the groove walls, for example. The spring element can be slid in the direction of the arrow 37 into the groove 36 at least to the point at which the arms 38, 39 plunge into the groove of the annular element 13", which is represented by the dashed base 40 of the groove. Since the spring element 19" automatically becomes wedged in the groove 36 of the guide element 15", it is also automatically fixed in the locked state.

The examples depicted in FIGS. 12 and 13 show that the locking between the guide element and the annular element can also be implemented without a deformable spring element and only by way of a spring element that can be displaced, rotated or pivoted.

Figure 14:
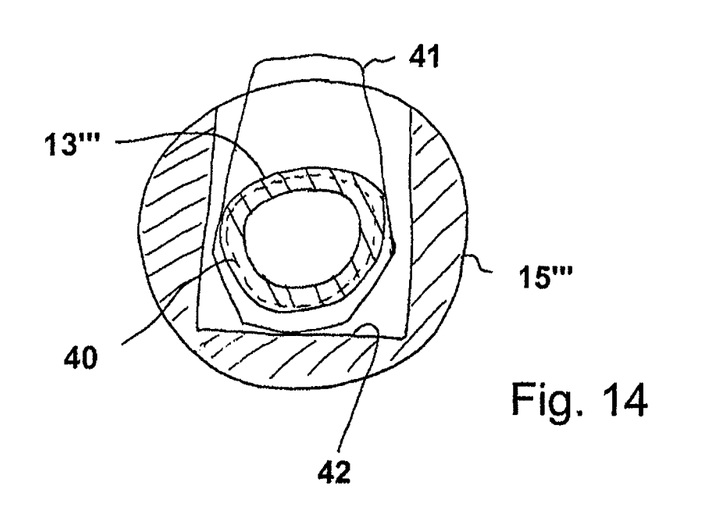
FIG. 14 a further guide element, in a cross section, comprising a spring element, FIG. 15 the design of a securing member, FIG. 16 a top view of a suture ring and FIG. 17 an alternative guide element comprising an upper part and a lower part, into which two snap-in spring elements plunge, and FIG. 18 an alternative guide element comprising an upper part and a lower part, in which a spiral spring element is accommodated.

FIG. 14 shows a guide element 15''' having a recess in which a spring element 41 can be moved radially against a fixed stop 42 of the guide element. The spring element 41 can be expanded beyond the outer contour of the annular element 13''' by applying pressure in the radial direction. In the locked state, the spring element plunges into the groove of the annular element 13''' to the base 40 thereof. The spring 41 protrudes radially from the guide element 15''' on one side for actuation.

Figure 15:
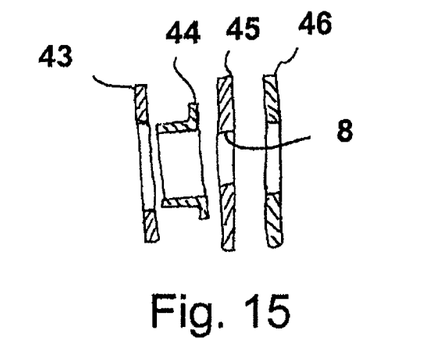

FIG. 15 shows the assembly of a securing member comprising, in the following axial order, a cloth ring 43, a suture ring 44 made of titanium and having an external flange, a silicone ring, the inner diameter of which is smaller than that of the remaining components, for forming a sealing lip 8 and a further cloth ring 46. The parts can be sutured and/or bonded to one another.

Figure 16:
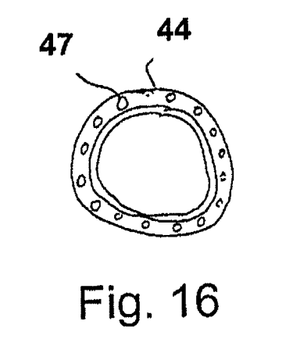

FIG. 16 shows a top view of the suture ring 44 comprising openings 47 in the external flange, which are provided for suturing.

Figure 17:
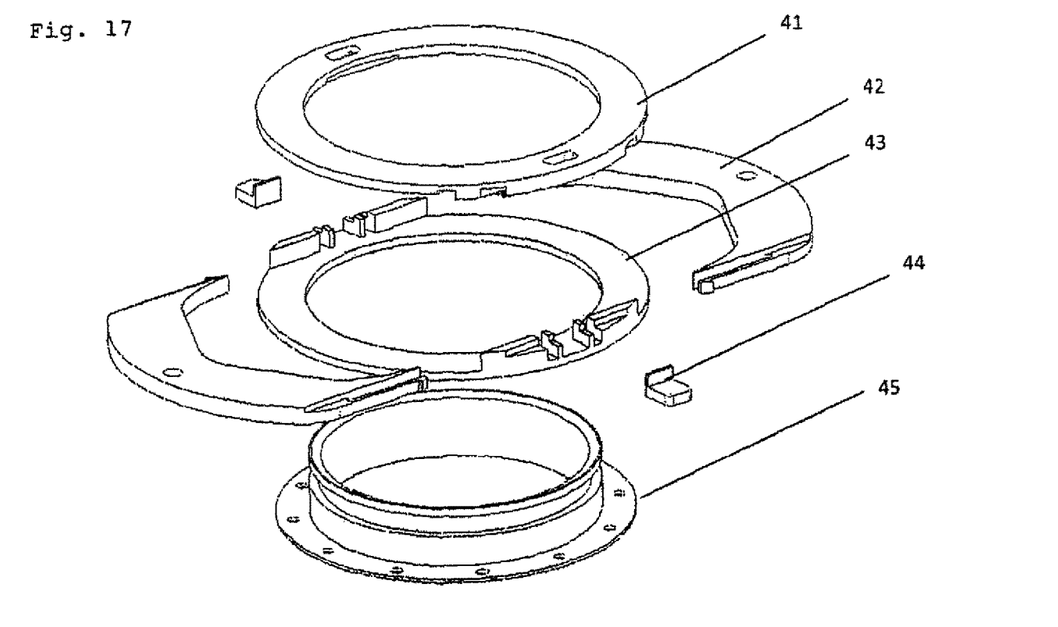

FIG. 17 shows a guide element comprising an upper part 41 and a lower part 43, into which two snap-in spring elements 42 plunge. These spring elements partially penetrate the circumferential groove of the annular element 45 and thereby lock the guide element and the annular element with respect to axial displacement. The spring elements snap into the locked position by way of snap-in hooks. The two snap-in hooks at the spring element are unlocked by applying pressure onto the two pressure pieces, thereby releasing the axial lock and permitting the spring elements to be removed from the groove.

Figure 18:
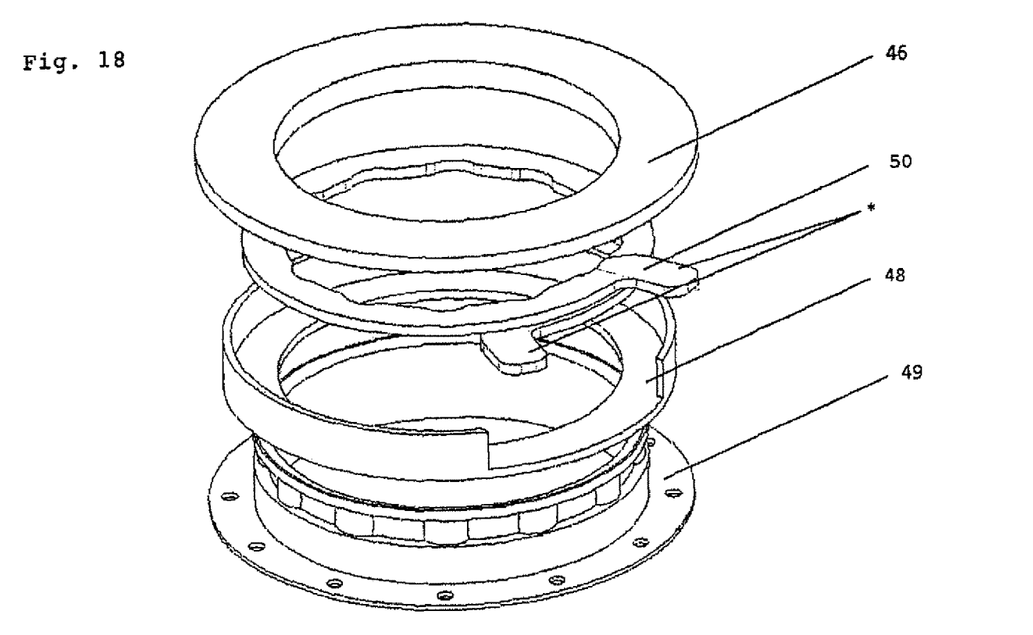

FIG. 18 shows an alternative guide element comprising an upper part 46 and a lower part 48, in which a spiral spring element 50 is accommodated. This spring element has recesses at the inner diameter. In the unloaded state, the spring element has a small diameter and plunges into the groove of the annular element 49 to secure it axially and tangentially.

By applying pressure to the points at the spring element indicated by *, the inner diameter of the spring element is increased to the extent that the annular element is axially and tangentially displaceable once more with respect to the guide element.

The implementations of the invention that are shown make it possible to easily and detachably connect a hollow cylindrical component 9 at an opening 2 in tissue of a patient's body, wherein the connection can be easily created even in surgical conditions and is fluid-tight. The hollow cylindrical component is easily rotated in the opening, optionally together with further elements secured thereto, such as pumps or valves.

The invention claimed is:

1. A connection system for detachably affixing a hollow cylindrical component at a recess in a part of a patient's body, the connection system comprising:
   an annular element that has a groove extending azimuthally around at least a section of an outer jacket surface of the annular element;
   the hollow cylindrical component; and
   a guide element, which can be displaced, before fixation, in the axial direction of the hollow cylindrical component with respect to the annular element, wherein the guide element and the annular element can be slid into one another at least partially in the axial direction, the guide element comprising a spring element, which is movably guided in the guide element exclusively perpendicular to the axial direction in both a connected and an unconnected state of the annular element and the guide element in such a way that, to establish a fixed state, the spring element plunges at least partially into the groove of the annular element and therefore mutually locks the annular element and the guide element in the axial direction, wherein, in both the connected and the unconnected state of the annular element and the guide element, the guide element and the spring element of the guide element are connected to the hollow cylindrical component, wherein, in the connected state, the hollow cylindrical component is inserted into an opening of the annular element, wherein the annular element is fixedly connected to a suture ring that is securable to organic tissue at an edge of the recess by way of a sutured connection using a thread.

2. The connection system according to claim 1, wherein the spring element is movably guided within the guide element without deformation of the spring element.

3. The connection system according to claim 1 or 2, wherein the spring element is elastically deformable within the guide element between a locked state and an unlocked state in which the spring element does not plunge into the groove of the annular element.

4. The connection system according to claim 1 or 2, wherein the spring element can be pressed at one side within the guide element radially with respect to the axial direction against a fixed stop, thereby permitting the spring element to expand radially.

5. The connection system according to claim 1 or 2, wherein the spring element protrudes on only one side beyond the guide element radially with respect to the axial direction and can be pressed radially from this side into the guide element.

6. The connection system according to claim 1 wherein the spring element comprises an elastically resilient component made of a plastic or a metal and is elastically expandable radially with respect to the axial direction of the hollow cylindrical component.

7. The connection system according to claim 1 wherein the spring element is an annularly closed, strand-shaped element.

8. The connection system according to claim 7, wherein expansion of the spring element is greater in a first direction than in a second direction that extends transversely to the first direction.

9. The connection system according to claim 7 or 8, wherein the spring element can be expanded by pressure directed radially toward a center of the spring element, said expansion extending transversely to the direction of the pressure.

10. The connection system according to claim 1, wherein the diameter of a circle inscribed in the spring element in the unloaded state is smaller than an outer diameter of the annular element.

11. The connection system according to claim 1, wherein the suture ring comprises a peripheral sealing lip at which the hollow cylindrical component extending therethrough seals.

12. The connection system according to claim 1, wherein the spring element is made entirely of an elastically resilient material and is elastically expandable radially with respect to the axial direction of the hollow cylindrical component.

13. The connection system according to claim 1, wherein the spring element includes two levers which are configured to load the spring when the two levers are pressed together.

14. The connection system according to claim 1, wherein the spring element comprises a spiral spring element.

15. The connection system according to claim 13, wherein the guide element comprises an upper part and a lower part in which the spiral spring element is accommodated and configured such that the spiral spring element plunges in the groove to secure the spiral spring element axially and tangentially in an unloaded state.

16. A connection system comprising:
   an annular element that has a groove extending azimuthally around at least a section of an outer jacket surface of the annular element;
   a hollow cylindrical component; and
   a guide element, which can be displaced, before fixation, in the axial direction of the hollow cylindrical component with respect to the annular element, wherein the guide element and the annular element can be slid into one another at least partially in the axial direction, the guide element comprising a spiral spring element, which is movably guided in the guide element exclusively perpendicular to the axial direction in both a connected and an unconnected state of the annular element and the guide element in such a way that, to establish a fixed state, the spring element plunges at least partially into the groove of the annular element and therefore mutually locks the annular element and the guide element in the axial direction, wherein, in both the connected and the unconnected state of the annular element and the guide element, the guide element and the spring element of the guide element are connectable to the hollow cylindrical component, wherein the annular element is fixedly connected to a suture ring that is securable to organic tissue at an edge of the recess by way of a sutured connection using a thread, and wherein the guide element comprises an upper part and a lower part in which the spiral spring element is accommodated and configured such that the spiral spring element plunges in the groove to secure the spiral spring element axially and tangentially in an unloaded state.

17. The connection system according to claim 16, wherein, in the connected state, the hollow cylindrical component is inserted into an opening of the annular element.

\* \* \* \* \*